United States Patent [19]
Ito

[11] 4,228,009
[45] Oct. 14, 1980

[54] TOROIDAL COIL PLANET CENTRIFUGE

[75] Inventor: Yoichiro Ito, Bethesda, Md.

[73] Assignee: The United States of America as represented by the Department of Health, Education and Welfare, Washington, D.C.

[21] Appl. No.: 45,052

[22] Filed: Jun. 4, 1979

[51] Int. Cl.³ .............................................. B01D 15/08
[52] U.S. Cl. ............................... 210/198 C; 210/322; 210/511; 233/14 R; 233/25
[58] Field of Search ................. 210/31 C, 198 C, 322, 210/511; 233/24, 25, 14 R

[56] References Cited
U.S. PATENT DOCUMENTS

| | | | |
|---|---|---|---|
| 3,775,309 | 11/1973 | Ito et al. | 210/198 C |
| 3,994,805 | 11/1976 | Ito | 210/198 C |
| 4,051,025 | 9/1977 | Ito | 210/198 C |
| 4,058,460 | 11/1977 | Ito | 210/198 C |

Primary Examiner—John Adee
Attorney, Agent, or Firm—Browdy and Neimark

[57] ABSTRACT

An apparatus for countercurrent chromatography consisting of a coiled separation column which is rotated about the axis about which is it wound and the axis is also rotated about a main axis. The embodiments of the invention are based on the fact that the pattern of the centrifugal force field greatly changes with the ratio of the two radii of rotation and depending on the particular effect desired, the apparatus is configured to achieve the most effective force field to gain the effect. The separation column is a tube helix wound around a flexible core member which can be wound onto the coil holder in various orientations to further effect the desired results.

12 Claims, 11 Drawing Figures

TOROIDAL COIL PLANET CENTRIFUGE

FIELD OF THE INVENTION

The present invention relates to centrifugal separation, and, more particularly, to toroidal coil centrifugation for the separation of particles and solutes from liquids.

BACKGROUND OF THE INVENTION

Centrifugal countercurrent chromatography has been used in high efficiency analytical separation with a variety of single and two phase systems. In separation it has been found that the geometry of the coiled column and the acting centrifugal force field play a major role in separation. In some of the previous art of toroidal coil centrifuge (for example see Y. Ito, U.S. Pat. No. 4,051,025, Sept. 27, 1977; also see Ito et al., Science 189, 999 (1975); Ito et al., Anal. Biochem. 85, 614 (1978); Sutherlund et al., Jour. High Resol. Chromatography and Chromatography Communications, 10019, 171 (1978); and Ito, Ser. No. 661,114), the coiled column is placed in the periphery of the rotating disc structure to produce a stable centrifugal force field where particles or stationary phase of a two-phase solvent system are retained in each coil unit favored by the acting direction of the force while the mobile phase is continuously eluted through the column. One of the disadvantages of this system is the lack of mixing force of the column contents which tends to produce inefficient separations.

Another type of system, called the horizontal flow-through coil planet centrifuge (e.g., see R. L. Bowman and Y. Ito, U.S. Pat. No. 3,775,309, Nov. 27, 1973; Ito et al., J. Chromotography, 147, 221 (1978); U.S. Pat. No. 3,994,805 Nov. 30, 1976 and Y. Ito, U.S. Pat. No. 4,058,460, Nov. 15, 1977), utilizes a coiled tube which synchronously rotates around its own axis in either the same or opposite direction while revolving about the central axis of the centrifuge. Thus planetary motion of the coiled column produces a rotating or oscillating centrifugal force field with respect to the coiled column.

However, satisfactory retentions of the stationary phases and particles often require a fine adjustment of this fluctuating acceleration field especially for partitions with polymer phase systems and cell separations. The above cited prior art devices have limited capabilities for this adjustment to meet efficient separations.

SUMMARY

It is, accordingly, an object of the invention to overcome deficiencies in the prior art; it is another object to provide for improved separation of materials.

A further object is to provide an improved system, and particularly an improved centrifugal apparatus, which utilizes a rotating coiled tube in a centrifugal force field for separation of particles and solutes.

Yet another object is to better control the pattern of the centrifugal force field to obtain improved separation.

BRIEF DESCRIPTION OF THE DRAWINGS

Further objects and advantages of the invention will become apparent from the following detailed description of the invention and from the accompanying drawings, in which.

DESCRIPTION OF THE DRAWINGS AND PREFERRED EMBODIMENTS

Figure 1A:
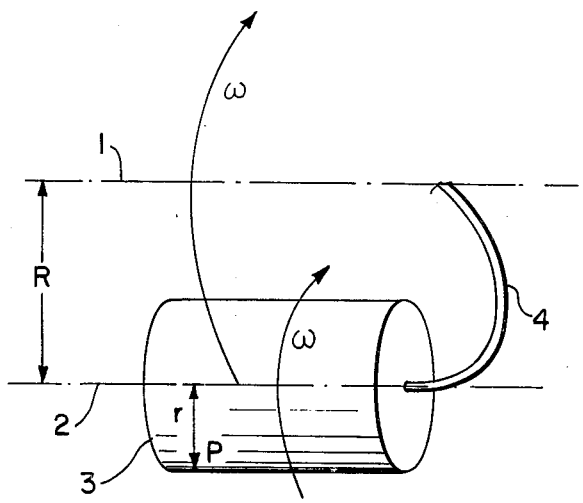
FIG. 1A is a diagrammatical perspective showing the relationship of the centers of rotation and revolution and the distance therebetween (R) as well as the radius of rotation (r)

To more fully understand the concepts involved in this invention, reference is had to FIG. 1A which shows a revolution axis 1, a rotation axis 2 which revolves around the axis 1, and a drum 3 which rotates about the axis 2. A tube 4 is shown connected to the drum 3 coaxial with the axis 2.

Figure 1B:
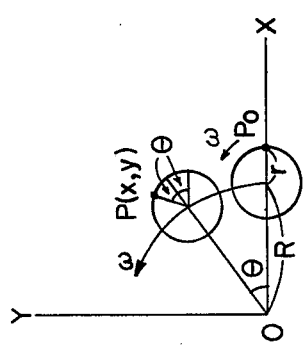
FIG. 1B is a coordinate system for analysis of the acceleration field acting on the arbitrary point P in FIG. 1A.

FIGS. 1B shows a coordinate system for analysis of acceleration field acting on the arbitrary point P, where the center of revolution is at point O, and the center of rotation and the point P are initially on the X-axis.

The following is an explanation of the symbols on FIG. 1 and others used herein:

P is an arbitrary point on drum 3;
R is the revolutional radius of drum 3, about the axis 1;
r is the rotational radius of point P about the axis 2;
w is the angular velocity of revolution;
$\theta$ is the angle of revolution of rotational center;
$\beta$ is r/R;
$\alpha$ is the net centrifugal acceleration field; and
$\gamma$ is the acting angle of acceleration with respect to the line drawn between the center of rotation and point P on the drum (or coil).

Analyses of the centrifugal force field shows that the pattern of the force field changes greatly with the ratio ($\beta$) of the two radii, r and R. An analysis of the net centrifugal acceleration field, $\alpha$ gives the following equation:

$$\alpha = Rw^2 (1 + 16\beta^2 + 8\beta \cos \theta)^{\frac{1}{2}} \tag{1}$$

The formula for the acting angle, $\gamma$, denoting the acceleration with respect to the line drawn between the center of rotation and point P is:

$$\gamma = \tan^{-1}\{(-\sin\theta)/(\cos\theta + 4\beta)\} \quad (2)$$

Figure 2:
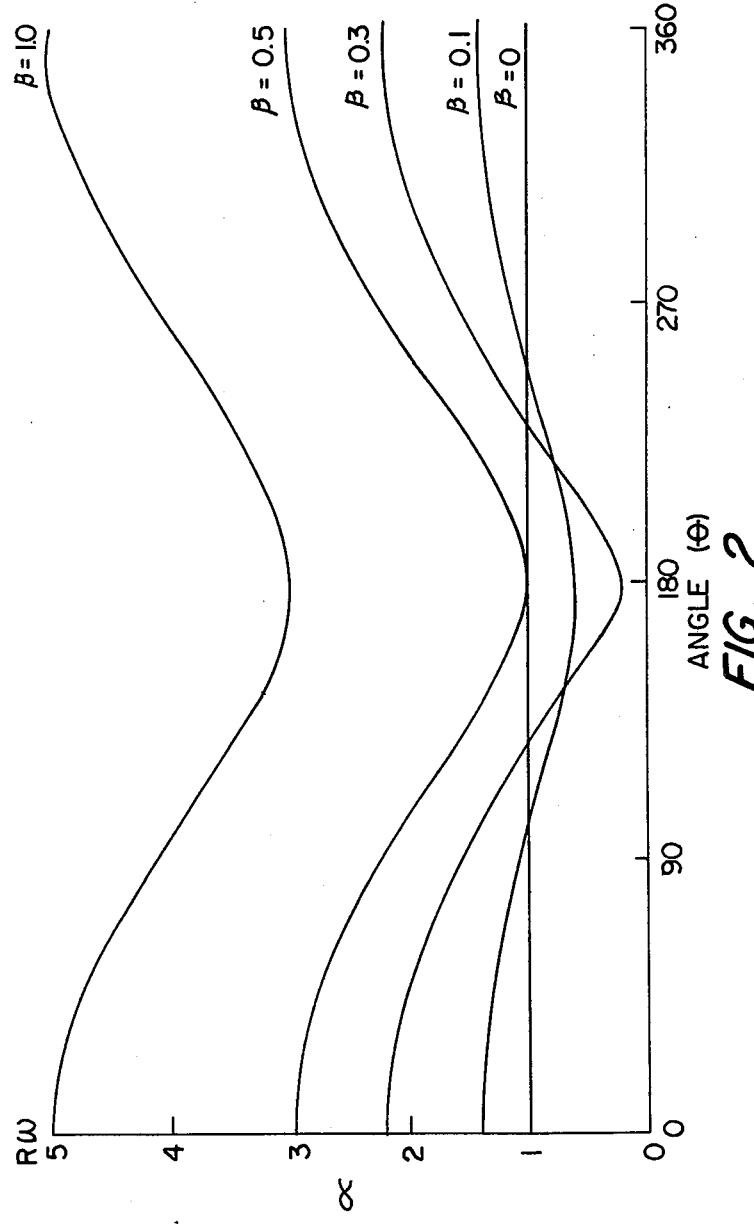
FIG. 2 is a graph showing the fluctuating magnitude of the acceleration field as a function of angle $\theta$, the angle of revolution of the rotational center relative to the X-axis, where $\beta = r/R$.
Figure 3:
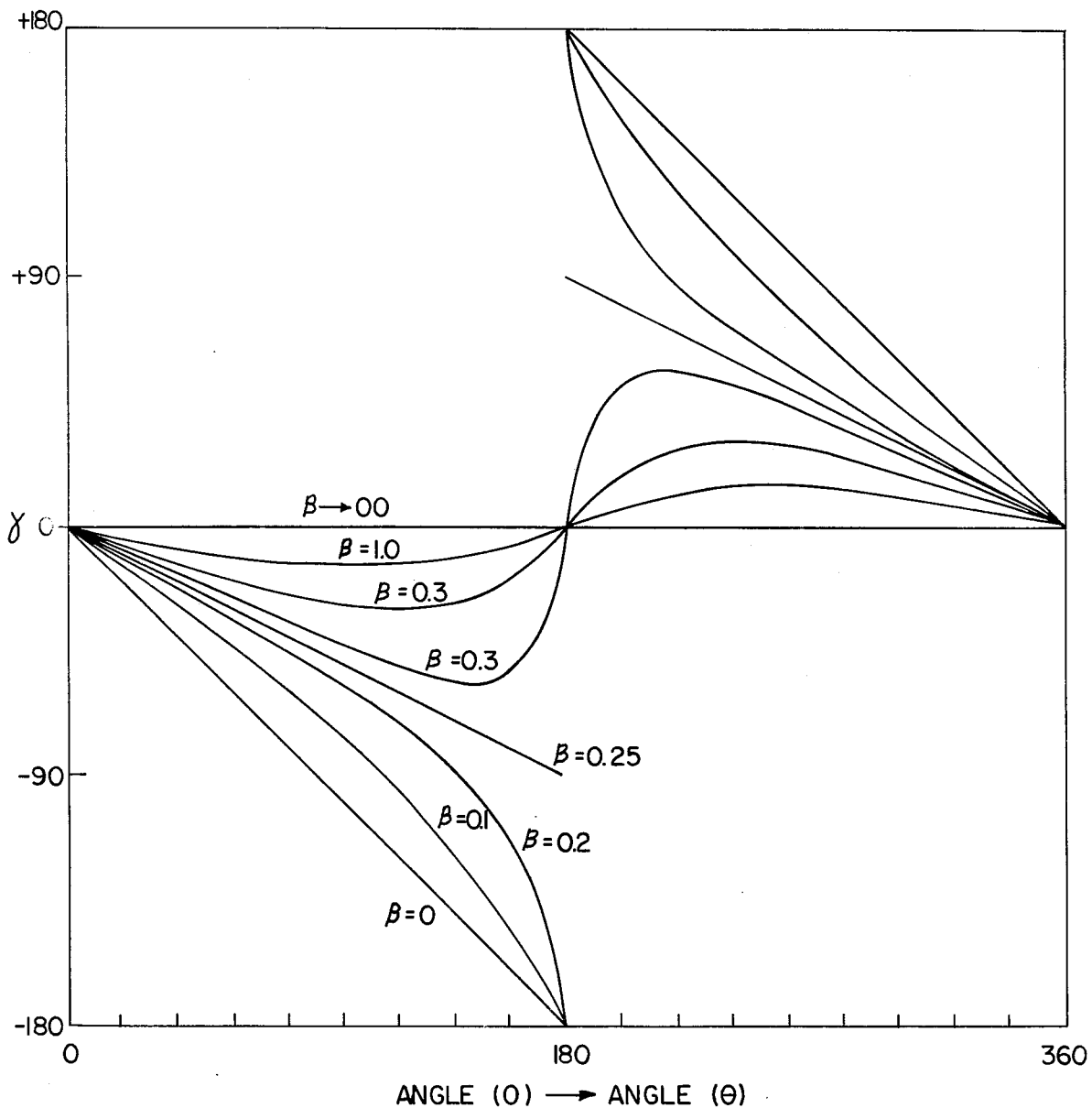
FIG. 3 is a graph showing the fluctuating direction of the acceleration vector as a function of the angle $\theta$, the angle of revolution of the rotational center, for different $\beta$ values.

The graph of FIG. 2 shows the fluctuating pattern of the acceleration field in magnitude. FIG. 3 shows the fluctuating pattern of the acceleration field in direction, or angle, ($\gamma$).

It should be noted that when $\beta$ values are smaller than 0.25, the acceleration field rotates around an arbitrary point. In cases where $\beta = 0$ or where P is on the axis of rotation 2, the field rotates uniformly around the point as in a flow-through coil centrifuge but in the opposite direction. The rotating acceleration field encourages the mixing of the contents while it quite often fails to retain light particles or low interfacial tension phase systems in the column.

As $\beta$ values rise in excess of 0.25, the rotation of the field changes into a swinging pattern, the amplitude of the angle decreasing with the larger $\beta$ values as seen in FIG. 3. This is significant in that the acceleration field always acts radially outward from the axis of the drum 3 or holder thus facilitating easy entrapment of the stationary phase or particles in each coil unit.

Figure 4:
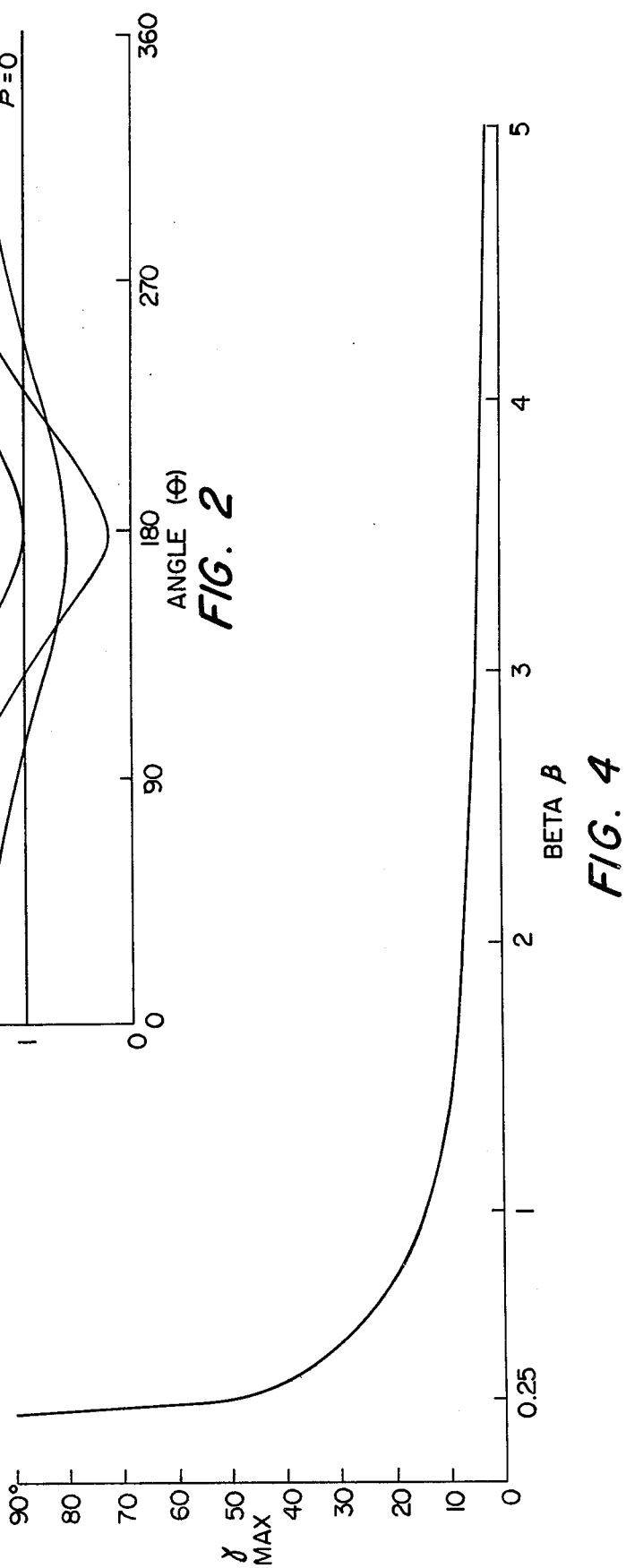
FIG. 4 is a graph showing the maximum amplitude of angle oscillation at various $\beta$ values.

With greater $\beta$ values, the magnitude of the net acceleration increases as shown in FIG. 2 while the amplitude of oscillation decreases as shown in FIG. 4. This provides for a stable retention of the contents of the coil. When $\beta$ is infinite or $R=0$, the system becomes identical to the prior art toroidal coil centrifuge where stability of coil contents is greatest.

The maximum amplitude of angle oscillation $\pm \gamma$ max at various values of $\beta$ is calculated from Equation 2 as:

$$\gamma\max = \tan^{-1}(16\beta^2 - 1)^{31\frac{1}{2}} \quad (3)$$

This is illustrated in FIG. 4 for various $\beta$ values. As shown, the amplitude sharply decreases with $\beta$ values which increase from 0.25 to 1.0.

From the above deductions and calculations the indication is clear that the $\beta$ value can be optimized for each set of separation requirements to attain the desired degree of mixing and retention of column contents.

An added consideration is the orientation of the coiled column with respect to the rotating drum. To overcome the difficulties in retention involved in separating light small particles and when using viscous low interfacial tension polymer phase systems, the coil can be oriented satisfactorily with respect to the acting acceleration field. The selection of relative orientation between the coiled column and the rotating drum is independent of the attitude of the apparatus, it being understood that the apparatus may be disposed for revolution and rotation of the drum about horizontal, vertical or angled axis.

Figure 5:
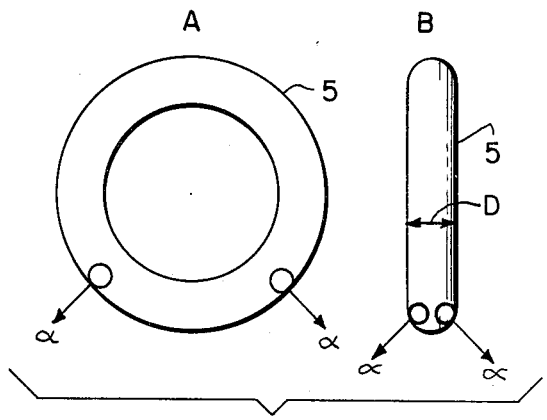
FIGS. 5A and 5B show the direction of centrifugal acceleration fields on coil contents when the coil is placed in the plane perpendicular to the axis of revolution and when it is oriented vertically to the plane, respectively.

As has been shown by the foregoing analysis, oscillation of the acceleration occurs in a plane perpendicular to the axis of revolution. Thus, if a coil 5 is oriented in the plane as schematically shown in FIG. 5A, the acceleration field mixes the contents of the coil along the length the coiled tube resulting in a superior mixing effect. Conversely, if the coil 5 is oriented perpendicularly to the plane, schematically shown as in FIG. 5B, all mixing will be limited and take place only in the space defined by the tube diameter D, the results being to stabilize the retention of the column contents.

Figure 6:
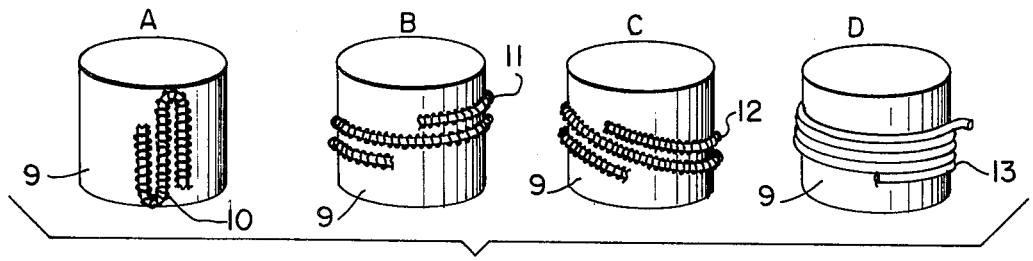
FIGS. 6A–6D are schematic perspective views of the coil mounted in various orientations to the rotating column support drum.
Figure 9:
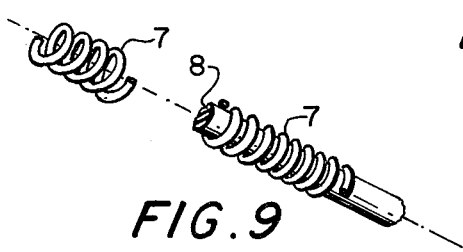
FIG. 9 is a schematic, exploded, partial perspective view of the coil and a core which is wound around the column support drum.

Referring to FIG. 9, a tube 7 is shown in a helix coiled tube with a flexible core member 8 around which it is wrapped. The core member 8 with the tubular column is then wrapped or mounted on the column support drum 9. In FIG. 6A the column 10 is wrapped on the support drum 9 to provide the perpendicular orientation described above and schematically shown in FIG. 5A. In FIG. 6B the column 11 and core 8 are shown wrapped onto the drum 9 to provide the orientation schematically depicted in FIG. 5B.

FIG. 6C shows column 12 with its flexible core wrapped around drum 9 at an angle between 0° and 90° to the plane perpendicular to the axis of rotation. Such an orientation provides a blend of mixing and retention characteristics.

If one is desirous of extreme agitation for mixing, the tube 13 is not coiled into a column but rather is wrapped directly onto the drum 9 as shown in FIG. 6D. Depending on the effects desired, any orientation, such as shown in FIGS. 6A–6D, may be selected.

Figure 10:
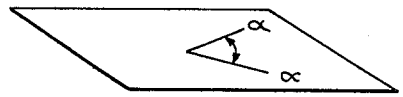
FIG. 10 is a diagrammatic view showing the acting centrifugal force field.

FIG. 10 shows the acting centrifugal force field on the plane perpendicular to the axis of rotation. It will now be seen that another object of the invention is to provide a coil planet centrifuge which gives a large $\beta$ value together with various orientations of the coil with respect to the acting centrifugal force field.

Figure 7:
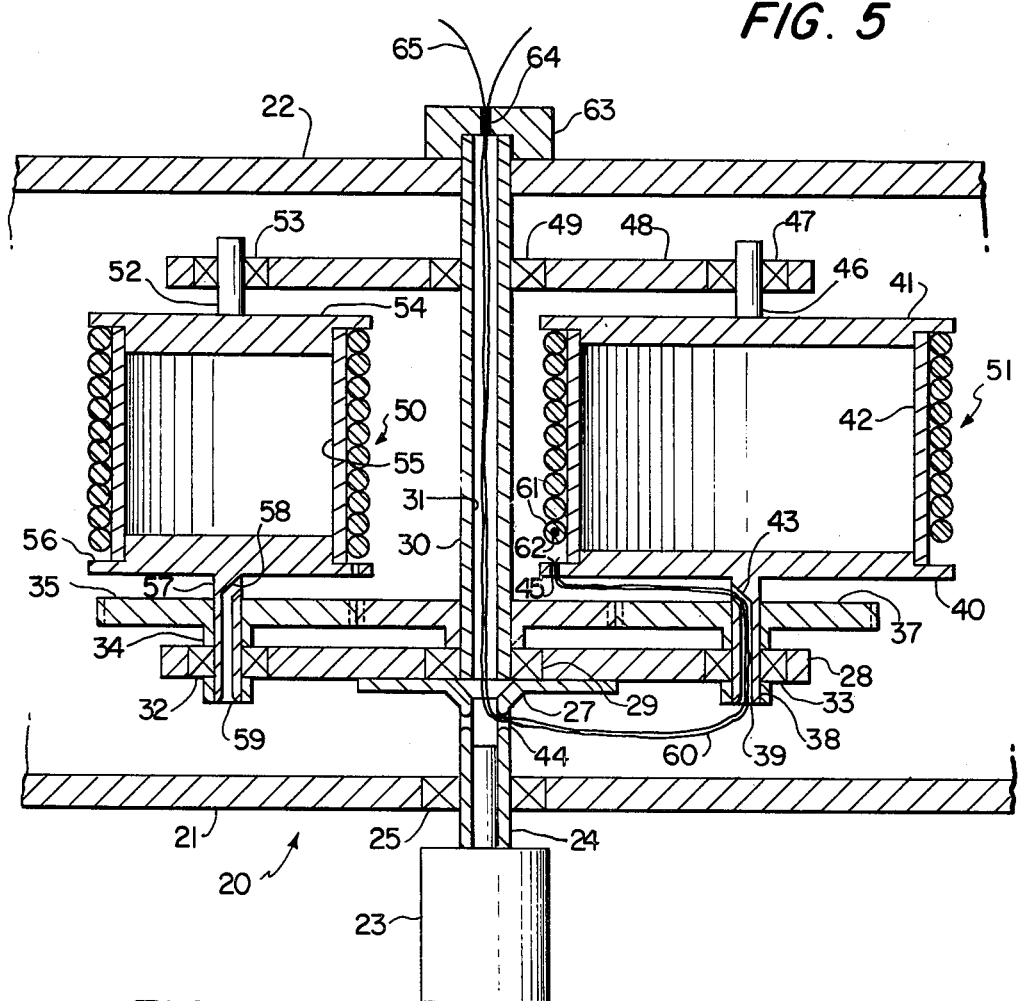
FIG. 7 is a transerve cross-section of an embodiment of this invention which provides $\beta$ values less than one.

Referring to FIG. 7 there is shown an embodiment 20 of the present invention which is designed to give $\beta$ value less than 1.0. The apparatus 20 comprises symmetrical coil holders 50, 51, mounted for rotative movement within a rotary frame 21, 22. The coil holders 50, 51 have different $\beta$ values, the coil holder 50 having a $\beta$ value of 0.5 and the coil holder 51 having a $\beta$ value of 0.75.

Generally, the apparatus 20 includes the upper and lower rigid frame members 21, 22 in which, revolves a rotary frame member having an upper rotary plate member 48 and a lower rotary plate member 28. The plate members 28, 48 are rigidly connected by a coupling collar or the like (not shown), i.e., they rotate together. A motor 23 drives a hollow shaft 24 through a bearing 25 supported by the lower frame 21. The shaft 24 is connected by wing members such as 27 to the lower rotary plate member 28 which, together with upper rotary plate member 48, revolves around a central stationary shaft member 30 on bearings 29, 49, respectively. The shaft member 30 has a hollow core which communicates with an opening(s) 44 in the hollow drive shaft 24.

The coil holder 51 has a top 41, a bottom 40, a cylindrical drum portion 42 and is mounted for rotation on an upper solid shaft 46 in the upper rotary plate member 48 through a bearing 47, and by a lower hollow shaft portion 38 in the plate member 28 through a bearing 33 and a planetary gear 37.

A flow tube 60 passes through a hole 64 in a cap member 63 in the upper frame 22 and into the bore 31 of the central stationary shaft member 30 and from there passes through the hole 44 to a hole 39 in the hollow shaft 38. The tube then passes through a slanted aperture 43 over to an aperature 45 in the flange of the bottom portion 40 of the holder 51. The coiled column is made by winding the tube 60 around a flexible core 62 as at 61.

The coil holder 50 and its attendant structure is similar to that described above with respect to holder 51. Thus, the holder 50 comprises a cylindrical shell 55 and upper and lower circular walls 54 and 56, with an upper shaft 52 passing through a bearing 53 in the plate member 48, and a lower hollow shaft 57 having a bore 59 and an aperature 58 passing through a bearing 32 in the plate member 28 and being keyed to a suitable gear 35 having an extension 34.

The planetary gears 35, 37 of holders 50 and 51 are fixed to shaft portions 57, 38 by keyways (not shown) for rotation therewith. The planetary gears engage a stationary or idler gear 36 which is fixed against rotation onto the central shaft 30. This arrangement provides for the desirable planetary motion of holders 50, 51 and prevents twisting of the flow tubes 60. Because of this arrangement the holders 50, 51 rotate on their own axes at the same velocity as the frame revolves around the shaft 31, and in the same direction. The relative movement keeps tube 60 correctly aligned against contorting. Usually, only one holder is used for separation at a time and the other serves as a counterbalance.

Figure 8:
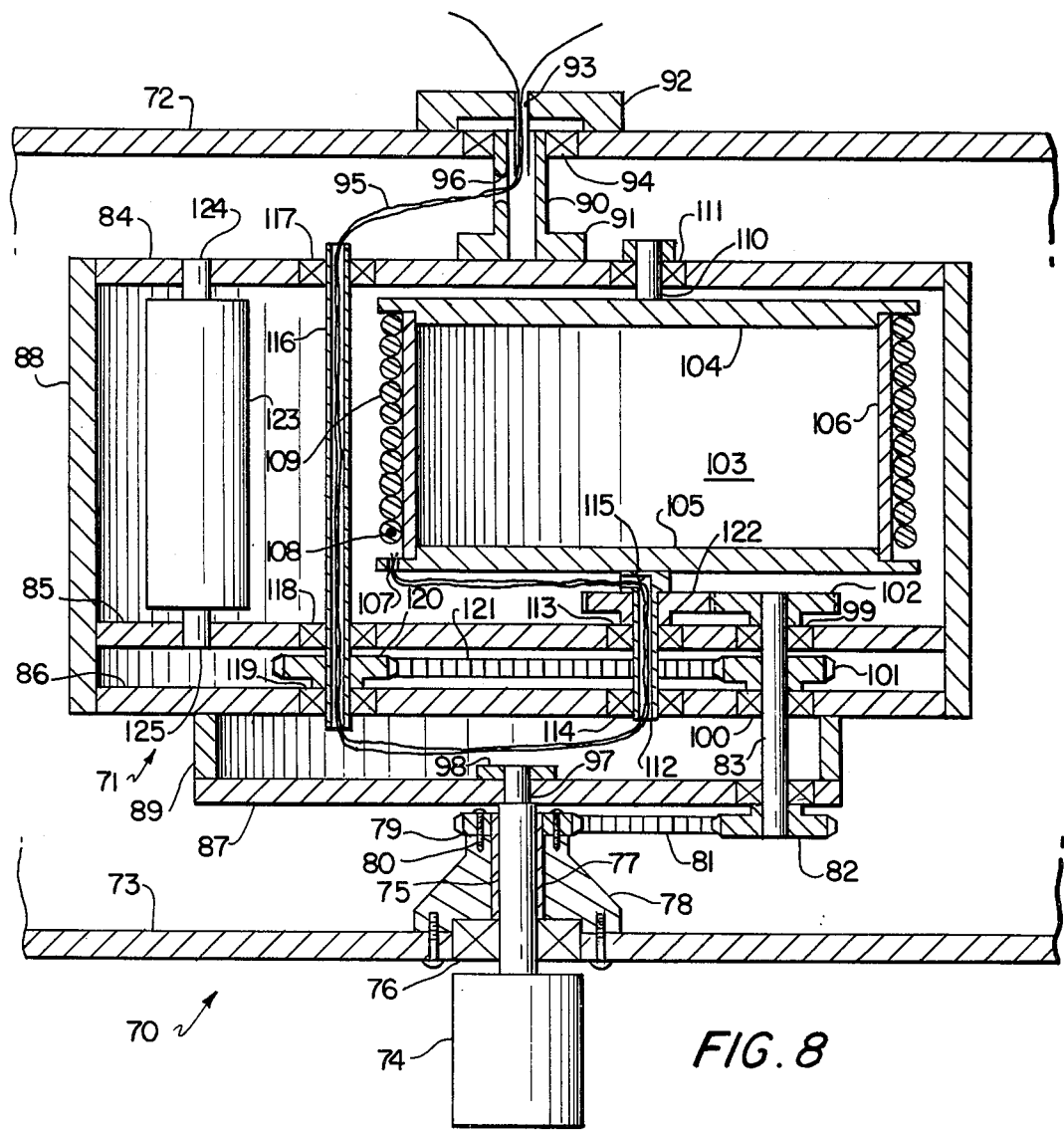
FIG. 8 is a transverse cross-section of another embodiment of this invention which provides $\beta$ values of greater than one.

To obtain a β value over 1, the apparatus 70 shown in FIG. 8, having a coil holder 103, is employed. In this embodiment the central stationary shaft used in the embodiment of FIG. 7 is eliminated. Within the apparatus 70 is provided a rotor frame 71 which is adapted to rotate.

The apparatus includes upper and lower main stationary members 72, 73, respectively, and a motor 74 adapted to drive a shaft 75, mounted for rotation in a bearing 76 and secured, by means of a washer 98 to the rotary frame 71 which rotates with the shaft 75 relative to the stationary member 73 having affixed thereto a gear support 78. A toothed pulley gear 79 is mounted atop the stationary gear support member 78 by bolts 80 and is adapted to drive a toothed belt 81 or the like, which in turn, drives a toothed pulley gear 82 affixed to a shaft 83.

The rotor frame 71 comprises four parallel plane plate members 84, 85, 86 and 87. Plate members 84, 85 and 86 are connected by a cylindrical wall member or multiple linking walls 88 and the plate member 87 is spaced from and secured to the plate member 86 by a cylindrical wall member or multiple linking walls 89. The upper plate member 84 is secured for rotative movement within the centrifuge 70 by an upper hollow shaft 90 which has a lower flange portion 91 secured to the plate member 84. A cap member 92, having an aperture 93, is affixed over a bearing 94 on the stationary frame member 72 and a flow tube 95 passes through the aperture 93 and shaft 90 and out through an aperture 96 therein.

The upper reduced portion 97 of the shaft 75 is secured to the plate member 87 as is a washer 98 thus facilitating rotary movement of the frame 71 by the motor 74. The shaft 83 is mounted for rotation in the plate members 85, 86 by suitable bushings 99, 100, respectively. Mounted for rotation with the shaft 83 and spaced between plate members 85, 86 is a toothed pulley gear 101, and at the upper end of the shaft 83 is secured a gear 102.

The coil holder 103 is mounted for rotary movement within the frame 71. It consists of upper and lower circular members 104, 105, respectively, and cylindrical wall member 106. Member 105 has an aperture 107 in the flange portion thereof through which the flow tube 95 passes prior to being wrapped around flexible member 108 to form windings of the double helix column around coil holder 103. Coil holder 103 is mounted via central upper shaft 110 and bearing 111 in plate member 84 for rotation relative thereto and via hollow shaft 112 and bearings 113 and 114, respectively, to plate members 85, 86. The flow tube 95 is fed up through shaft 112 and out an aperture 115 therein.

Hollow shaft 116 is mounted for relative rotative movement with frame 71 by bearings 117, 118 and 119. A toothed pulley gear 120 is secured to shaft 116 and is driven by toothed belt 121 which, in turn, is driven by pulley gear 101. It should be noted that much of the structure provided serves to protect the tubing 95 from undue wear; however, when the tubes 95 are intended to be disposed after only a short period of use this protection is not necessary and the apparatus can be constructed without the hollow shaft 116, bearings 117, 118 and 119, pulleys 120 and 101, and toothed belt 121. Affixed to hollow shaft 112 for rotation therewith is gear 122 which is driven by gear 102 in a 1:1 relationship.

A counterweight 123 having shaft portions 124, 125 is secured to plate members 84, 85 of frame 71.

From this arrangement coil holder 103 synchronously rotates around its own axis on rotating frame 71 in the same direction. The pulley gears 120 and 101 with belt 121 counterrotate hollow shaft 116 thus maintaining the flow tube 95 free of twisting and obviating the need for a rotating seal.

The tube 95 can be a single tube or can be multiple tubes passing through shafts 90, 112 and 116 which are then wound around flexible core member 108 to form a double helix column. The configuration shown in FIG. 8 results in a β value of 2.

In either of the embodiments, both single phase and two phase solvent systems can be employed. When using the apparatus for particle separation using a single phase solvent, the column is initially filled with the solvent and particle suspension is introduced into the column. The solvent is then pumped at a desired rate while the apparatus is rotated at a desired speed. The eluate is fractionated into test tubes using the fraction collector for later analysis.

When using two-phase solvent systems in the partition technique, the coiled column is first filled with the stationary phase, either upper or lower phase, of an equilibrated two phase solvent system and the sample solution is introduced into the column. Elution of the mobile phase follows while the apparatus is rotated at a desired speed. The eluate can be continuously monitored if desired, e.g. by a spectrophotometer, and fractionated with a fraction collector as in conventional chromatographic techniques.

While two specific embodiments of an improved apparatus for countercurrent chromatography have been disclosed in the foregoing description, it will be understood that various modifications within the scope of the invention may occur to those of ordinary skill in the art. It is therefore intended that adaptations and modifications should and are intended to be comprehended within the meaning and range of equivalents of the disclosed embodiments.

What is claimed is:

1. A toroidal coil planet centrifuge, comprising:
   a support means provided with upper and lower stationary members;
   rotary frame means provided with upper and lower plate portions and mounted between said stationary members for rotation about a first vertical axis;

at least one coil means mounted between said upper and lower plate members around a second vertical axis, said second vertical axis being spaced from said first vertical axis by distance R, and said coil holder means having a substantially cylindrical separation column supporting surface spaced from said second axis by distance r, the ratio of r to R being greater than 0.25;

separation column means mounted on said coil holder supporting surface, said separation column means including a flexible core member and at least one tube having ends at least one tube wound in a helix about said flexible core member;

inlet and outlet tubes connected to respective said ends of said at least one tube;

tube holding means located within said rotary frame means for holding said inlet and outlet tubes so that the orientation thereof remains constant;

drive means for rotating said frame means and said coil holder means; and counterbalancing means mounted on said frame means opposite said coil holder means.

2. A centrifuge as in claim 1, wherein said counterbalancing means comprises a second coil holder means mounted opposite said first coil holder means for rotation about a third vertical axis.

3. A centrifuge as in claim 1, wherein the ratio of r to R is greater than 0.25 and less than 1.0.

4. A centrifuge as in claim 1, wherein the flexible core member is wound around the coil holder supporting surface in a substantially horizontal orientation.

5. A centrifuge as in claim 1, wherein the flexible core member is affixed to the coil holder supporting surface in a substantially vertical orientation.

6. A centrifuge as in claim 1, wherein the flexible core member is affixed to the coil holder supporting surface in an orientation between horizontal and vertical.

7. A centrifuge as in claim 1, wherein said drive means includes a motor in operative engagement with planetary gear means which are in operative engagement with solid coil holder means to thereby rotate said coil holder means and thereby said frame means.

8. A centrifuge as in claim 1, wherein said counterbalancing means comprises a counterweight mounted opposite said coil holder between said upper and lower plate members for free rotative movement.

9. A centrifuge as in claim 1, wherein the ratio of r to R is greater than 1.0.

10. A toroidal coil planet centrifuge, comprising:

a support means provided with upper and lower stationary members;

rotary frame means provided with upper and lower plate portions and mounted between said stationary members for rotation about a first vertical axis;

at least one coil holder means mounted between said upper and lower plate members around a second vertical axis, said second vertical axis being spaced from said first vertical axis by distance R, and said coil holder means having a substantially cylinderical separation means supporting surface spaced from said second axis by distance r, the ratio of r to R being greater than 0.25;

separation means mounted on said coil holder supporting surface, said separation means including at least one tube wrapped directly onto said cylinderical supporting surface and having two ends;

inlet and outlet tubes connected to respective said ends of said at least one tube;

a tube holding means located within said rotary frame means for holding said inlet and outlet tubes so that the orientation thereof will remain constant;

drive means for rotating said frame means and coil holder means; and counterbalancing means mounted on said frame means opposite said coil holder means.

11. A centrifuge as in claim 10, wherein the ratio of r to R is greater than 0.25 and less than 1.0

12. A centrifuge as in claim 10, wherein the ration of r to R is greater than 1.0.

* * * * *